(12) United States Patent
Telandro

(10) Patent No.: US 10,758,413 B2
(45) Date of Patent: Sep. 1, 2020

(54) FEMTO SECOND MULTI SHOOTING FOR EYE SURGERY

(71) Applicant: CESACAR PARTICIPACIONS, S.L., Barcelona (ES)

(72) Inventor: Alain Telandro, Cannes (FR)

(73) Assignee: CESACAR PARTICIPACIONS, S.L., Barcelona (ES)

( * ) Notice: Subject to any disclaimer, the term of this patent is extended or adjusted under 35 U.S.C. 154(b) by 0 days.

(21) Appl. No.: 14/650,283

(22) PCT Filed: Dec. 6, 2013

(86) PCT No.: PCT/IB2013/003190
§ 371 (c)(1),
(2) Date: Jun. 5, 2015

(87) PCT Pub. No.: WO2014/087250
PCT Pub. Date: Jun. 12, 2014

(65) Prior Publication Data
US 2015/0313760 A1 Nov. 5, 2015

Related U.S. Application Data

(60) Provisional application No. 61/734,914, filed on Dec. 7, 2012.

(51) Int. Cl.
*A61F 9/008* (2006.01)

(52) U.S. Cl.
CPC .......... *A61F 9/008* (2013.01); *A61F 9/00825* (2013.01); *A61F 9/00827* (2013.01);
(Continued)

(58) Field of Classification Search
CPC .. A61F 9/008; A61F 9/00825; A61F 9/00829; A61F 9/00827; A61F 9/00838;
(Continued)

(56) References Cited

U.S. PATENT DOCUMENTS

| | | |
|---|---|---|
| 4,550,022 A | 10/1985 | Garabedian et al. |
| 5,207,668 A * | 5/1993 | L'Esperance, Jr. ........................ A61F 9/00804 606/5 |

(Continued)

FOREIGN PATENT DOCUMENTS

| | | |
|---|---|---|
| EP | 1132065 A1 | 9/2001 |
| EP | 2914301 A2 | 9/2015 |

(Continued)

OTHER PUBLICATIONS

Schmut O. "The Organization of tissues of the eye by different collagen types." Aug. 16, 1978, Albrecht Von Graefes Arch Klin Exp Opthalmol; 207 (3); 189-99.*

(Continued)

*Primary Examiner* — Lynsey C Eiseman
*Assistant Examiner* — Jessandra F Hough
(74) *Attorney, Agent, or Firm* — Wilson Sonsini Goodrich & Rosati

(57) ABSTRACT

Provided herein are methods for non-invasive ophthalmic surgery based on femto second multi shooting (FSMS) laser techniques. In one embodiment the FSMS laser technique is directed to corneal stroma. In another embodiment the FSMS laser technique is directed to crystalline lens.

10 Claims, 15 Drawing Sheets

Single and multi-shots Femto second laser in Corneal stroma

Multi-shots occurred opacity

(52) U.S. Cl.
CPC ...... *A61F 9/00829* (2013.01); *A61F 9/00838* (2013.01); *A61F 2009/0087* (2013.01); *A61F 2009/00872* (2013.01); *A61F 2009/00893* (2013.01); *A61F 2009/00895* (2013.01)

(58) Field of Classification Search
CPC .... A61F 2009/0087; A61F 2009/00872; A61F 2009/00893; A61F 2009/00895; G01G 19/414; G01G 19/50; A61B 5/02007; A61B 5/02125; A61B 5/02416; A61B 5/0295; A61B 5/0535; A61B 5/1036; A61B 5/1102; A61B 5/6892; A61B 5/7278

See application file for complete search history.

(56) References Cited

U.S. PATENT DOCUMENTS

| | | | |
|---|---|---|---|
| 5,792,103 | A | 8/1998 | Schwartz et al. |
| 6,218,428 | B1 | 4/2001 | Chynn |
| 6,663,619 | B2 | 12/2003 | Odrich et al. |
| 2003/0014021 | A1 | 1/2003 | Holmen et al. |
| 2003/0232287 | A1* | 12/2003 | Bango ................ G03F 7/20 430/321 |
| 2004/0199149 | A1* | 10/2004 | Myers ................ A61F 9/008 606/4 |
| 2008/0089918 | A1 | 4/2008 | Lebreton |
| 2009/0171327 | A1* | 7/2009 | Kurtz ................ A61B 18/20 606/6 |
| 2010/0286770 | A1* | 11/2010 | Tomalla ............ A61F 2/147 623/5.12 |
| 2011/0160622 | A1* | 6/2011 | McArdle .......... A61F 9/00825 601/2 |
| 2011/0160712 | A1* | 6/2011 | Tankovich ........ A61B 18/203 606/9 |
| 2011/0206071 | A1 | 8/2011 | Karavitis |
| 2013/0253402 | A1 | 9/2013 | Badawi et al. |
| 2015/0029775 | A1 | 1/2015 | Ravasio et al. |
| 2015/0297755 | A1 | 10/2015 | Telandro |

FOREIGN PATENT DOCUMENTS

| | | |
|---|---|---|
| EP | 2928426 A2 | 10/2015 |
| WO | WO-2014072831 A2 | 5/2014 |
| WO | WO-2014087250 A2 | 6/2014 |

OTHER PUBLICATIONS

Majumder P. "Anatomy of Lens." http://www.eophtha.com/eophtha/Anatomy/anatomyoflens.html.*
Chernyak and Campbell, System for the design, manufacturing, and testing of custom lenses with known amounts of high-order aberrations. J.Opt.Soc.Am. A., 20(11):2016-2021 (2003).
Schwiegerling, Custom photorefractive keratectomy ablations for the correction of spherical and cylindrical refractive error and higher-order aberration. J.Opt.Soc.Am. A, 12(9):2572-2579 (1998).
Gwon et al., Focal laser photophacoablation of normal and cataractous lenses in rabbits: Preliminary report. J.Cataract Refract. Surgery, 21:282 (1995).
Jimenez et al., Equation for corneal asphericity after corneal refractive surgery. Journal of Refractive Surgery, 19:65-69 (2003).
Krueger et al., Experimental increase in accommodative potential after neodymium: Yttrium-aluminum-garnet laser photodisruption of paired cadaver lenses. Ophthalmology, 108:2122-2129 (2001).
Lin, Critical review on refractive surgical lasers. Optical Engineering, 34(3): 668-675 (1995).
Manns et al., Albation profiles for wavefront-guided correction of myopia and primary spherical aberration. J.Cataract Refract. Surgery, 28:766-774 (2002).
Marcos, Aberrations and visual performance following standard laser vision correction. Journal of Refractive Surgery, 17:S596-S601 (2001).
Moreno-Barriuso et al., Ocular aberrations before and after myopic corneal refractive surgery: Lasik-induced changes measured with laser ray tracing. Investigative Ophthalmology & Visual Science, 42(6): 1396-1403 (2001).
Munnerlyn et al., Photorefractive keratectomy: A technique for laser refractive surgery. J.Cataract Refract. Surgery, 14:46 (1988).
Ryan and Logani, Nd:YAG laser photodisruption of the lens nucleus before phacoemulsification. American Journal of Ophthalmology, 104:382-386 (1987).
Chinese Patent Application No. 2013800690960 First Office Action dated Dec. 15, 2016.
Chinese Patent Application No. 201380072518X First Office Action dated May 5, 2016.
Chinese Patent Application No. 201380072518X Second Office Action dated Mar. 29, 2017.
Shestopalov et al. Three-Dimensional Organization of Primary Lens Fiber Cells. Invest Ophthalmol Vis Sci 41(3):859-863 (2000).
Song et al. Functions of the intermediate filament cytoskeleton in the eye lens. JCI 19(7):1837-1848 (2009).
Sridhar. Anatomy of cornea and ocular surface. Indian J. Ophthalmol 66(2):190-194 (2018).
Wride et al. Lens fibre cell differentiation and organelle loss: many paths lead to clarity. Philos Trans R Soc Lond B Biol Sci. 366(1568):1219-1233 (2011).
Chinese Patent Application No. 201380072518X Office Action dated Dec. 15, 2017.
European Patent Application No. 13844552.3 Office Action dated Apr. 20, 2018.
Hosney et al., Fluorescein-assisted viscodissection for easier phacoemulsification. International Ophthalmology. p. 257-258 (2001) Retrieved from the internet: URL:http://www.ncbi.nlm.nih.gov/pubmed/14531626.
Takahashi et al., Two cases of intraoperative anterior chamber angle observation using ophthalmic endoscope in viscocanalostomy. American Journal of Ophthalmology. 138(6):1060-1063 (2004).
Uka et al., Endoscope-aided cataract surgery in corneal opacity associated with aniridia. Journal of Cataract and Refractive Surgery. 31(7):1455-1456 (2005).
U.S. Appl. No. 14/440,336 Office Action dated Jun. 8, 2018.
Chinese Patent Application No. 2013800690960 second Office Action dated Nov. 10, 2017.
PCT/IB2013/003099 International Preliminary Report on Patentability dated May 5, 2015.
PCT/IB2013/003099 Written Opinion and International Search Report dated Jun. 26, 2014.
Indian Patent Application No. 4619/DELN P/2015 Examination report under sections 12 & 13 of the Patents Act 1970 and the Patents Rules 2003 dated Jan. 10, 2020.
Marcos et al., Optical response to LASIK surgery for myopia from total and corneal aberration measurements. Invest. Ophthalmol. Vis. Sci., 42:3349-3356 (2001).
Liu et al.: Development of an Ex Vivo Method for Evaluation of Precorneal Residence of Topical Ophthalmic Formulations; AAPS PharmSciTech; vol. 10, No. 3: 796-805 (2009).
U.S. Appl. No. 14/440,336 Final Office Action dated May 2, 2019.

* cited by examiner

Single and multi-shots Femto second laser in Corneal stroma

Multi-shots occurred opacity

FSMS in hyperopic and hyperopic astigmatism

1. Hyperopic

2. Hyperopic Astigmatism
(+2)180°

FSMS to treat myopic ametropia

Low Myopic Case

- T2
- Optical Zone = free of impact
- Transition Zone
- Treatment

High Myopic Case

- Treatment
- T2
- O2
- T8

FSMS to treat myopic astigmatism

1. (-2) 90°

- OVAL O2
- Symmetrical or asymmetrical
- Couple effect Treatment

2. -2(-2) 180°

Electronic microscopy of the cellular layers of crystalline lens

Germinative zone of crystalline lens

Less coehcs de & de mine age
sant dlepaincur indentigue

Volume tranfert during accomodation

Transfert de Volume pendant le accommodation

Sliding assumption of thikned cells

Hypothese gleiscusent - epaississement

Clinical Analyse

Hydro dissection operative

Relation of clevage plan of lens and age during cataract surgery

Selou flage at a degree de Cataracte

Microscopic strategy

Increase of dellamination diameter by successive laser shoot

FEMTO SECOND MULTI SHOOTING FOR EYE SURGERY

CROSS-REFERENCE

This application is filed pursuant to 35 U.S.C. § 371 as a United States National Phase Application of International Application No. PCT/IB2013/003190, filed on Dec. 6, 2013, which claims the benefit of U.S. Ser. No. 61/734,914, filed Dec. 7, 2012, the contents of which are incorporated herein by reference in their entirety.

BACKGROUND OF THE INVENTION

Approximately 60 percent of Americans have refractive errors, and millions of people are myopic worldwide. Many thousands of laser refractive surgeries are performed every year for the correction of myopia. These procedures will ultimately affect a large number of individuals around the globe, and yet the corneal response to laser ablation is not well understood. Of the many individuals treated, about 15-50% do not achieve 20/20 vision which translates into very large patient numbers when the extremely high popularity of refractive surgery is considered. It is crucial that the number of patients who achieve their targeted vision be increased in order to improve the overall quality of vision in this vast group of people.

Anterior corneal surface topography cannot take into account contributions of optically important structures inside the eye, such as the posterior corneal surface and the crystalline lens. If a laser were programmed strictly with anterior topography data, the correction would be at best incomplete, and at worst simply wrong. Therefore, wavefront analysis is important, particularly if the ultimate goal is to correct higher order aberrations along with the sphere and cylinder.

Refractive errors are traditionally compensated both with ophthalmic lenses and with contact lenses. As an alternative to these correction methods, corrective surgical procedures of the incisional type, such as radial keratotomy, appeared in the '80s. They have recently been replaced by photorefractive keratectomy (PRK) and laser assisted in-situ keratomileusis (LASIK) which modify the shape of the cornea in order to thereby change its power and compensate the refractive errors. These last two procedures use an excimer laser for forming the cornea in order to remove tissue by means of ablation. While in PRK surgery the ablation commences on the surface layers of the cornea (first the epithelium and then the Bowman layer), in LASIK surgery those layers are not ablated since a microkeratome creates a surface lamina of corneal tissue which is removed prior to the ablation and replaced afterwards so that just the stroma is ablated.

SUMMARY OF THE INVENTION

The present invention relates to methods for eye surgery wherein coloration is incorporated in ophthalmic surgical procedures.

The present invention relates to non-invasive ophthalmic surgery incorporating femto second multi shooting (FSMS) laser techniques.

In one embodiment the FSMS laser technique is employed during refractive eye surgery.

In another embodiment the FSMS laser surgery is used on the corneal stroma, where laser shoots result in microvacuoles of gas and changes in the density of the corneal stroma, decreasing the links between collagen fibers and increasing the plasticity of the cornea.

In one embodiment the FSMS laser technique is X63 nm.

In one embodiment the FSMS laser is used for treating corneal aberrations.

In one embodiment the FSMS laser is used for myopic treatment.

In one embodiment the FSMS laser is used for hyperopic treatment.

In one embodiment the FSMS laser is used for hyperopic astigmatic treatment.

In one embodiment the FSMS laser is used for myopic astigmatic treatment.

In one embodiment the FSMS laser is used for presbyopia treatment by creation of a central myopic island.

In one embodiment the FSMS laser is used for keratoconus treatment.

In another embodiment of the invention the FSMS laser is used for improving non-invasive crystalline lens surgery comprising of:

The use of femto second multi shooting laser technique of X63 nm

In one embodiment the FSMS laser treatment without incision on crystalline lens.

In one embodiment the FSMS laser treatment without incision on the lens capsule.

In one embodiment using the FSMS laser on the lamellar structure of the crystalline lens.

In one embodiment using the FSMS laser for accommodation of the crystalline lens.

In one embodiment using the FSMS laser for accommodation by macroscopic strategy.

In an alternate embodiment using the FSMS laser for accommodation by microscopic strategy.

In another embodiment using the FSMS laser for accommodation on the lens core.

In yet another embodiment using FSMS laser for presbyopia treatment.

In another embodiment using the FSMS laser for phaco rejuvenation to eliminate opacity of the crystalline lens.

In an alternate embodiment using the FSMS laser for femto-phaco rejuvenation before the cataract stage.

In another embodiment using the FSMS laser for phaco delamination.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
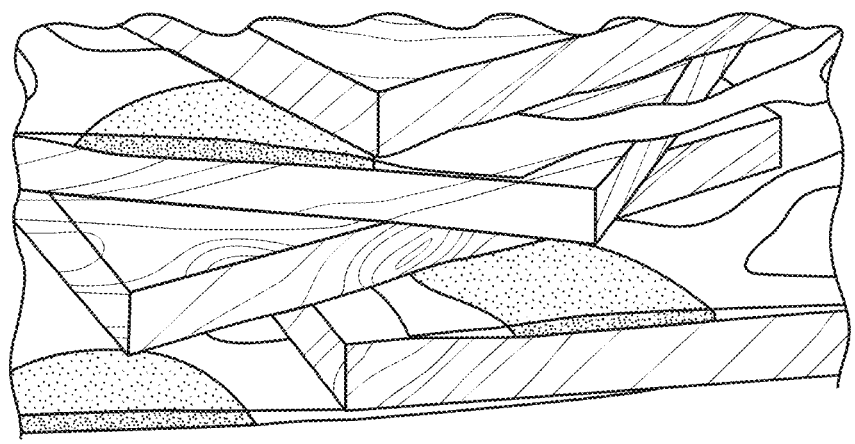
FIG. 1: shows arrangement of the collagen fibril in corneal stroma.
Figure 1:
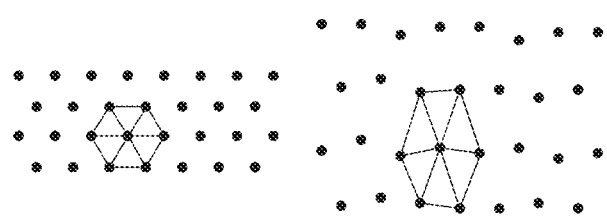

Provided herein are methods for eye surgery wherein coloration is incorporated in ophthalmic surgical procedures. The present invention relates to non-invasive ophthalmic surgery incorporating femto second multi shooting (FSMS) laser techniques. In one embodiment the FSMS laser technique is employed during refractive eye surgery. In another embodiment the FSMS laser surgery is used on the corneal stroma, where laser shoots result in microvacuoles of gas and changes in the density of the corneal stroma, decreasing the links between collagen fibers and increasing the plasticity of the cornea.

In refractive procedures known as standard, the ablation pattern is based on the Munnerlyn function (Munnerlyn C, Koons S, Marshall J. Photorefractive keratectomy: technique for laser refractive surgery. J Cataract Refract Surg 1988; 14:46-52), whose values are the ablation depths at each point of the cornea. The Munnerlyn function is the subtraction of two spherical surfaces representing the corneal surfaces before and after the ablation. The difference in powers of both spheres is the power that is wished to correct. The Munnerlyn ablation pattern can be used for correction of myopia (reducing the power of the cornea) and for the correction of hypermetropia (increasing the power of the cornea). This ablation pattern can also be used for correction of astigmatism by introducing a meridional dependence on power into the Munnerlyn function. A parabolic equation is frequently used as an approximation to the Munnerlyn function (Jiménez J, Anera R, Jiménez del Barco L. Equation for corneal asphericity after corneal refractive surgery. J Refract Surg. 2003:65-69; Lin J. Critical review on refractive surgical lasers. Optical Engineering 1995; 34:668-675). Said parabolic formula is obtained by truncating the Taylor expansion of the Munnerlyn function.

As well as the Munnerlyn and parabolic ablation patterns, other ablation patterns have been proposed that are defined with biconic surfaces (Schwiegerling J, Snyder R. Custom photorefractive keratectomy ablations for the correction of spherical and cylindrical refractive error and higher-order aberration. Journal of the Optical Society of America A 1998; 15:2572-2579) or with individual optical aberrations (personalized ablation patterns: Manns F, Ho A, Parel J, Culbertson W. Ablation profiles for wavefront-guided correction of myopia and primary spherical aberration. J Cataract Refract Surg 2002; 28:766-774). Moreover, ablations with multifocal algorithms have been proposed and carried out (Odrich N, Greenberg K, Legerton J, Munnerlyn C, Schimrnick J. Method and systems for laser treatment of presbyopia using offset imaging. U.S. Pat. No. 6,663,619; VISX. Incorporated, 2003). The ablation pattern designed with biconic surfaces, as well as the apical radii of curvature, considers corneal asphericities in such a way that permits control not just of the change of power but also of the corneal asphericity after the ablation (and therefore the spherical aberration). Corneal asphericity is defined as the asphericity Q of the conic surface $x^2+y^2+(1+Q)z^2-2zR=0$ which provides the best fit for the conical surface, where R is the apical radius of curvature and (x,y,z) are Cartesian coordinates. The average asphericity of pre-operative corneas is slightly negative (Q=−0.26), indicating greater curvature in the centre of the cornea than in the periphery. This asphericity provides a slightly positive conical spherical aberration, which tends to be compensated in young subjects with the negative spherical aberration of the lens. A cornea that is free of spherical aberration would have an asphericity of 0.52 (Atchison D A, Smith G. Optics of the Human Eye. Oxford: Butterworth-Heinemann, 2000). The personalized ablation pattern exploits the possibility offered by flying spot excimer laser systems of eliminating tissue asymmetrically. Based on the prior measurement of the patient's map of ocular aberrations, this in theory permits a pattern to be formed on the cornea such that post-operative ocular aberrations approximate to zero. Algorithms of this type have been proposed for the manufacture by means of flying spot excimer laser systems of customized phase plates or contact lenses for the correction of the patient's ocular aberrations (Chernyak D, Campbell C.). Systems for the design, manufacture, and testing of custom lenses with known amounts of high-order aberrations (JOSA A 2003:20; 2016-2021). For this, account has to be taken of the differences in refractive index of the cornea and of the plastic material used Algorithms are currently starting to be applied which produce a multifocal ablation pattern for use in patients with presbyopia (loss of focusing capacity which affects the entire population starting from the age of 45).

Clinical experience shows that PRK and LASIK surgery in general satisfactorily eliminate the conventional refractive errors of patients. Nevertheless, it has been experimentally demonstrated that spherical aberration is significantly increased (a factor of close to 4 on average in a group of patients with 22 D) with standard LASIK refractive surgery for myopia (Moreno-Barriuso E, Merayo-Lloves J, Marcos S., et al.). Ocular aberrations before and after myopic conical refractive surgery: LASIK-induced changes measured with Laser Ray Tracing (Invest. Oph. Vis. Sci. 2001: 42; 1396-1403). This increase is mainly produced in the cornea (Marcos S, Barbero B, Llorente L, Merayo-Lloves J.; Optical response to LASIK for myopia from total and corneal aberration measurements, Invest. Oph. Vis. Sci. 2001:42; 3349-3356) and produces a diminution in the visual function in terms of sensitivity to contrast (Marcos S. Aberrations and Visual Performance following standard laser vision correction. J. Refract. Surgery 2001:17:596-601) which manifests itself in the form of nocturnal halos and other visual artifacts which can sometimes be very annoying to the patient.

Photodisruptive laser technology can deliver laser pulses into the lens to optically fragment the lens without insertion of a probe and thus can offer the potential for improved lens removal. Laser-induced photodisruption has been widely used in laser ophthalmic surgery and Nd:YAG lasers have been frequently used as the laser sources, including lens fragmentation via laser induced photodisruption. Some existing systems utilize nanosecond lasers with pulse energies of several mJ (E. H. Ryan et al. American Journal of Opthalmology 104: 382-386, October 1987; R. R. Kruger et al. Opthalmology 108: 2122-2129, 2001), and picosecond lasers with several tens of mJ (A. Gwon et al. J. Cataract Refract Surg. 21, 282-286, 1995). These relatively long pulses deposit relatively large amounts of energy into the surgical spots, resulting in considerable limitations on the precision and control of the procedure, while creating a relatively high level of risk of unwanted outcomes.

In parallel, in the related field of cornea surgery it was recognized that shorter pulse durations and better focusing can be achieved by using pulses of duration of hundreds of femtosecond instead of the nanosecond and picosecond pulses. Femtosecond pulses deposit much less energy per pulse, significantly increasing the precision and the safety of the procedure.

Presently several companies commercialize femtosecond laser technology for ophthalmic procedures on the cornea, such as LASIK flaps and corneal transplants. These companies include Intralase Corp./Advanced Medical Optics, USA, 20/10 Perfect Vision Optische Gerate GmbH, Germany, Carl Zeiss Meditec, Inc. Germany, and Ziemer Ophthalmic Systems AG, Switzerland, Alcon.

However, these systems are designed according to the requirements of the cornea surgery. Crucially, the depth range of the laser focus is typically less than about 1 mm, the thickness of the cornea. As such, these designs do not offer solutions for the considerable challenges of performing surgery on the lens of the eye.

Eye Surgery Procedures:
The refractive surgery for the cornea to treat myopia, astigmatism, hypermetropy, presbyopia are a) Fiodorov method with incision to produce a biomechanical modification. b) Surgery with ablation without laser based on Baraquer's, Krumeisch's, Swinguer's methods. c) Biomechanical method using Intracor's Femto second laser described by Ruiz and Technolas. d) KAMRA inlay for age related presbyopia.
Surgery for the crystalline lens is conducted using: a) ICL™ Phakic implantable intraocular lenses. b) IOL Toric and multifocal intraocular lens implants, pseudophakic. c) Biomechanical approach using Femto second laser with incisions.
Scleral buckle is one of the lens rejuvenation techniques: a) Band expansion using Schachard's scleral surgery. b) Alain Telandro's scleral surgery using excimer laser ablation.
Mixed or bioptic eye surgeries combining two different techniques.

The methods provided herein pertain to improving visual quality through refractive surgery using the concept of femto multi shooting on the cornea or on the lens. The approach of this work to surgery on either the corneal or on the crystalline lens, is to distribute multiple femto second laser pulses separated from each other, without creating incisions, but by acting by structural modification of the corneal stroma or the lens fibers, with appropriately spaced laser pulses taking advantage of the anatomical structure of the cornea or of the ageing crystalline lens.

Femto second laser shoots create micro vacuoles or micro cavities on the tissues of cornea or the lens without any incision and with no modification on the lens transparency. These "showers" of femto second laser impact and modify the biomechanics of the biological target, in this case the cornea, lens or both with no photo ablation. This technique gives a better than one micron surgery precision compared to existing techniques with a corneal incision giving a precision of hundreds of microns.

FMSF

I. Provided herein are methods based on femto second laser multi shooting (FSMS) with no incision on the cornea based on the anatomical features of the cornea.

1. First: X63 nm

The human cornea has five layers. From the anterior to posterior the five layers of the human cornea are:
A. Corneal epithelium: an exceedingly thin multicellular epithelial tissue layer (non-keratinized stratified squamous epithelium) of fast-growing and easily regenerated cells, kept moist with tears. Irregularity or edema of the corneal epithelium disrupts the smoothness of the air/tear-film interface, the most significant component of the total refractive power of the eye, thereby reducing visual acuity.
B. Bowman's layer: a tough layer that protects the corneal stroma, consisting of similar irregularly arranged collagen fibers, mainly type I collagen fibrils, essentially a type of stroma.
C. Corneal stroma: a thick, transparent middle layer, consisting of regularly arranged collagen fibers along with sparsely distributed interconnected keratocytes, which are the cells for general repair and maintenance. They are parallel and are superimposed like book pages. The corneal stroma consists of approximately 200 layers of mainly type I collagen fibrils. Each layer is 1.5-2.5 µm. Up to 90% of the corneal thickness is composed of stroma. There are two theories of how transparency in the cornea comes about:
a) The lattice arrangements of the collagen fibrils in the stroma. The light scatter by individual fibrils is cancelled by destructive interference from the scattered light from other individual fibrils. (Maurice, 1957) FIG. 1.
b) The spacing of the neighboring collagen fibrils in the stroma must be <200 nm for there to be transparency. (Goldman and Benedek)
A. Descemet's membrane: a thin, highly transparent acellular layer that serves as the modified basement membrane of the corneal endothelium, from which the cells are derived. This layer is composed mainly of collagen type IV fibrils, less rigid than collagen type I fibrils.
B. Corneal endothelium: approx 5 µm thick, of mitochondria-rich cells. These cells are responsible for regulating fluid and solute transport between the aqueous and corneal stroma compartments. Unlike the corneal epithelium the cells of the endothelium do not regenerate. Instead, they stretch to compensate for dead cells reducing the overall cell density of the endothelium and have an impact on fluid regulation. If the endothelium can no longer maintain a proper fluid balance, stroma swelling due to excess fluids and subsequent loss of transparency will occur and this may cause corneal edema and interference with the transparency of the cornea and thus impairing the image formed.

The corneal stroma is a collagen stratified on parallel slides, each slide is covering the corneal surface with a different orientation. During the impact of the femto second laser there is a formation of micro vacuoles that needs to be balanced. One shoot of the femto second laser disturbs the frequency, same disturbance in collagen structure can happen with a bad frequency multi shoots.

Figure 2:
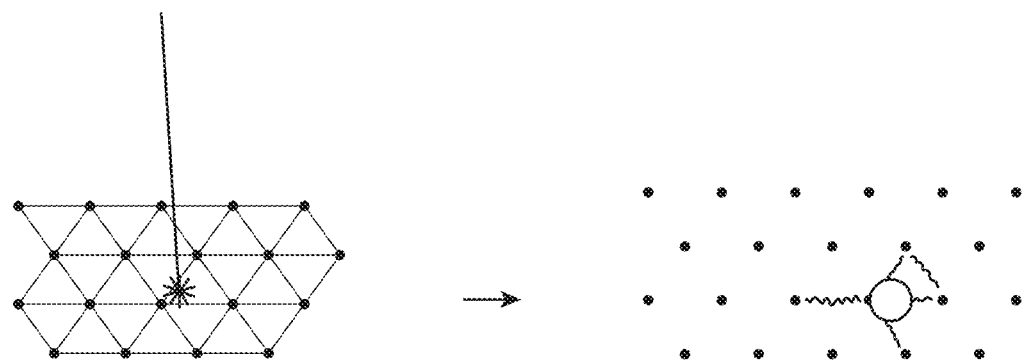
FIG. 2: shows single and multi shoots femto second laser in corneal stroma.
Figure 2:
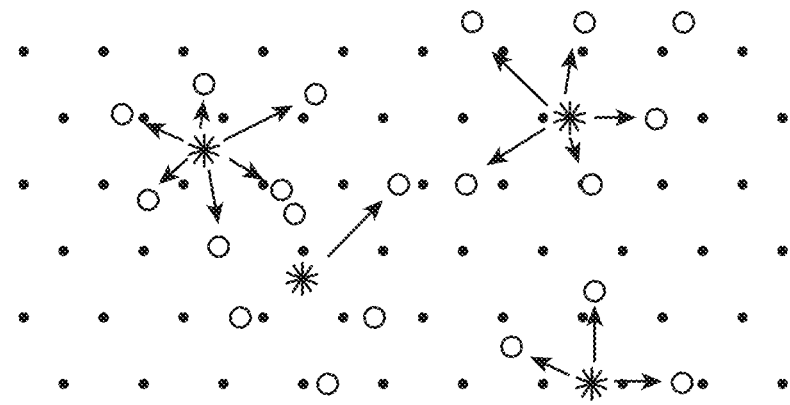

FIG. 2 is a representation of single and multiple shoots of the femto second laser in the corneal stroma.

Figure 3:
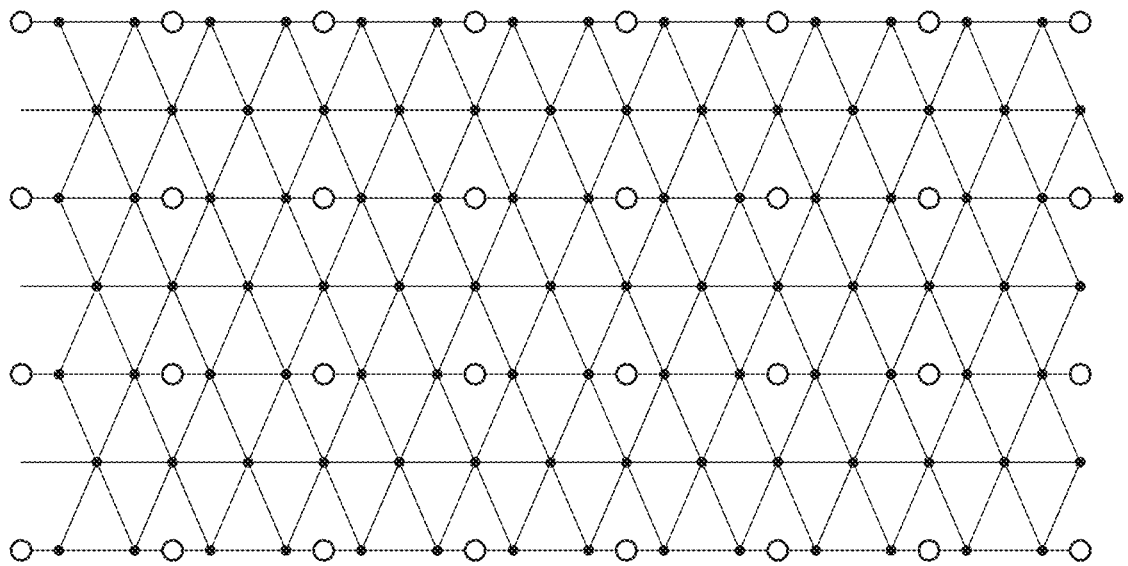
FIG. 3: shows FSMS (femto second laser multi shoots) X63 nm on corneal stroma.

The stratification of the Type 1 collagen filament with diameter of 32 to 34 nm and the periodicity of the lamellar collagen structure of 62 nm to 64 nm is the basis for X63 nm. Using X63 nm femto second laser multi shoots, allows to formation of the micro vacuoles to be x times 63 nm separated from each other in 3 dimension. In this way each spot will be balanced by the effect of the surrounding shoots. The density of the cornea stroma changes and keeps the general structure balanced and keeps the transparency of the cornea. The reduction of links number between each fibers of collagen increases the plasticity and reduces the mechanical resistance to the IOP. FIG. 3 represents the femto second laser of X63 nm.

Density variation of impacts to the depth in the cornea allows modulating type of the eye treatment.

Figure 4:
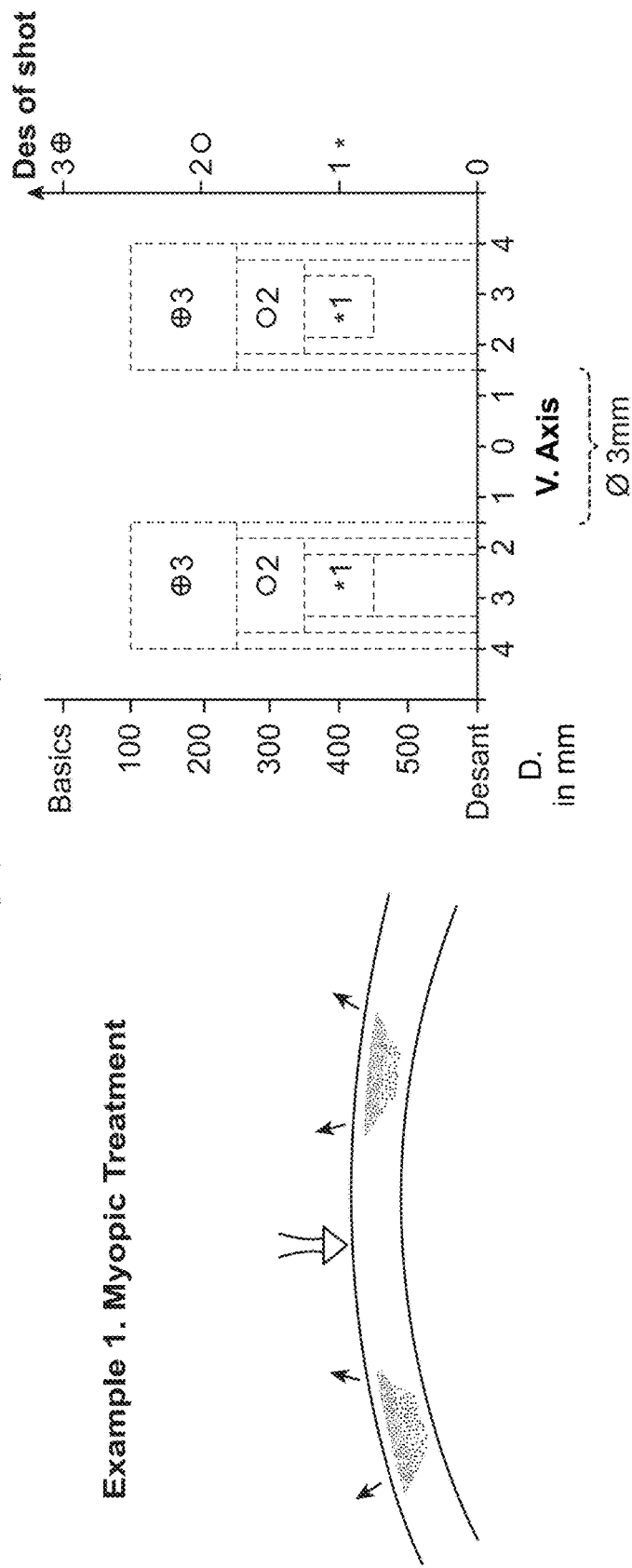
FIG. 4: illustrates FSMS treatment for myopic treatment.

FIG. 4 it is an example of a myopic treatment, where the femto second laser shoots are distributed on the surface than the depth of the corneal stroma with a density of bottom to upwards.

Figure 5:
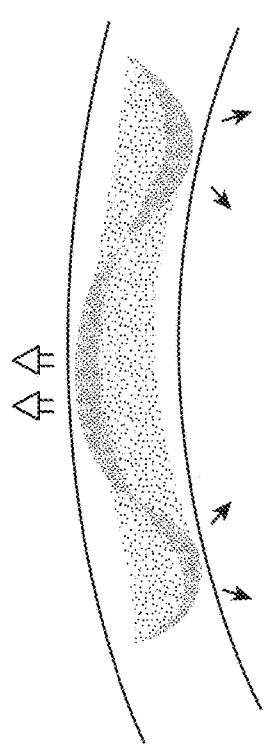
FIG. 5: illustrates FSMS treatment for hyperopic treatment.

FIG. 5 presents an example of the treatment for farsightedness where the density of femto second shoots lies within the surface center and its periphery.

2. Effect of myopia and increase of the keratometric value of the cornea: The Mode M.

One way to control the effect is to create an ectasia on the optic zone to increase the K value. The treatment with FSMS is done by choosing a sector of various shapes and size such as ring, circle, triangle or arc. The treated surface increases its K value, so in this case the treatment has a direct effect on the focus by steepening the central cornea. This is a basic method to treat hyperopic ametropia.

Figure 6:
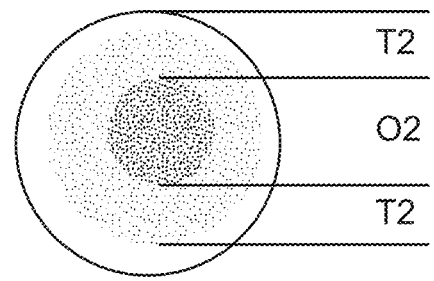
FIG. 6: illustrates FSMS X63 nm hyperopic treatment.
Figure 7:
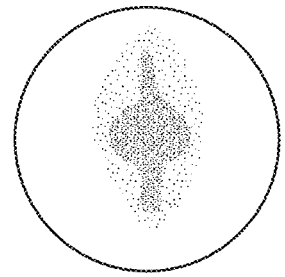
FIG. 7: illustrates FSMS treatment for hyperopic astigmatism.

FIG. 6 presents FSMS shoots for hyperopic astigmatism and FIG. 7 shows the organization of FSMS shoots for hyperopic astigmatism.

3. Hypermetropic affect with decrease of keratometric value of the cornea: The Mode H.

Figure 8:
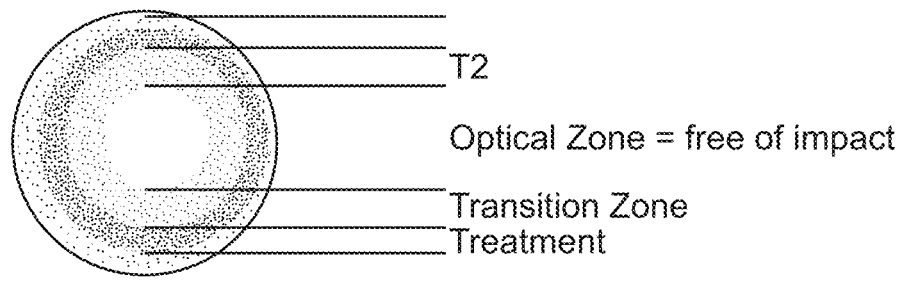
FIG. 8: illustrates FSMS to treat myopic ametropia.
Figure 8:
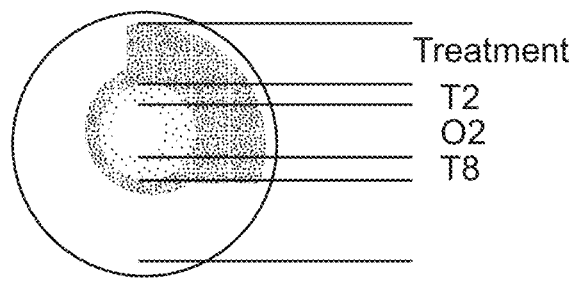

FIG. 8 describes how to treat myopic ametropia with FSMS shoots with an increase of K of an external ring treated surface will decrease and flatten the central area like the initial radial keratotomy Fiodoro. In low myopic condition secondary to the stability of the diameter of the cornea is equivalent to limbus circle stable structure. In high myopic condition secondary to the stability of the surface of the cornea, there is no elasticity of the collagen fibers.

Figure 9:
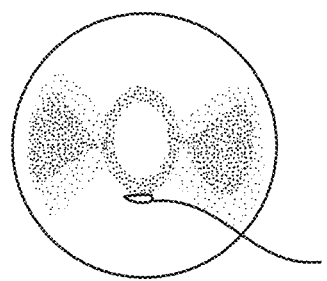
FIG. 9: illustrates FSMS to treat myopic astigmatism.
Figure 9:
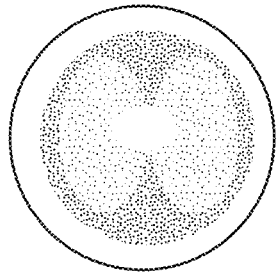

FIG. 9 is a description of the FSMS use in treating myopic astigmatism.

4. Treatment of presbyopia with FSMS by creating an central myopic island, this way a multi focal cornea can be created to generate a corneal pseudo-accommodation.

Figure 10:
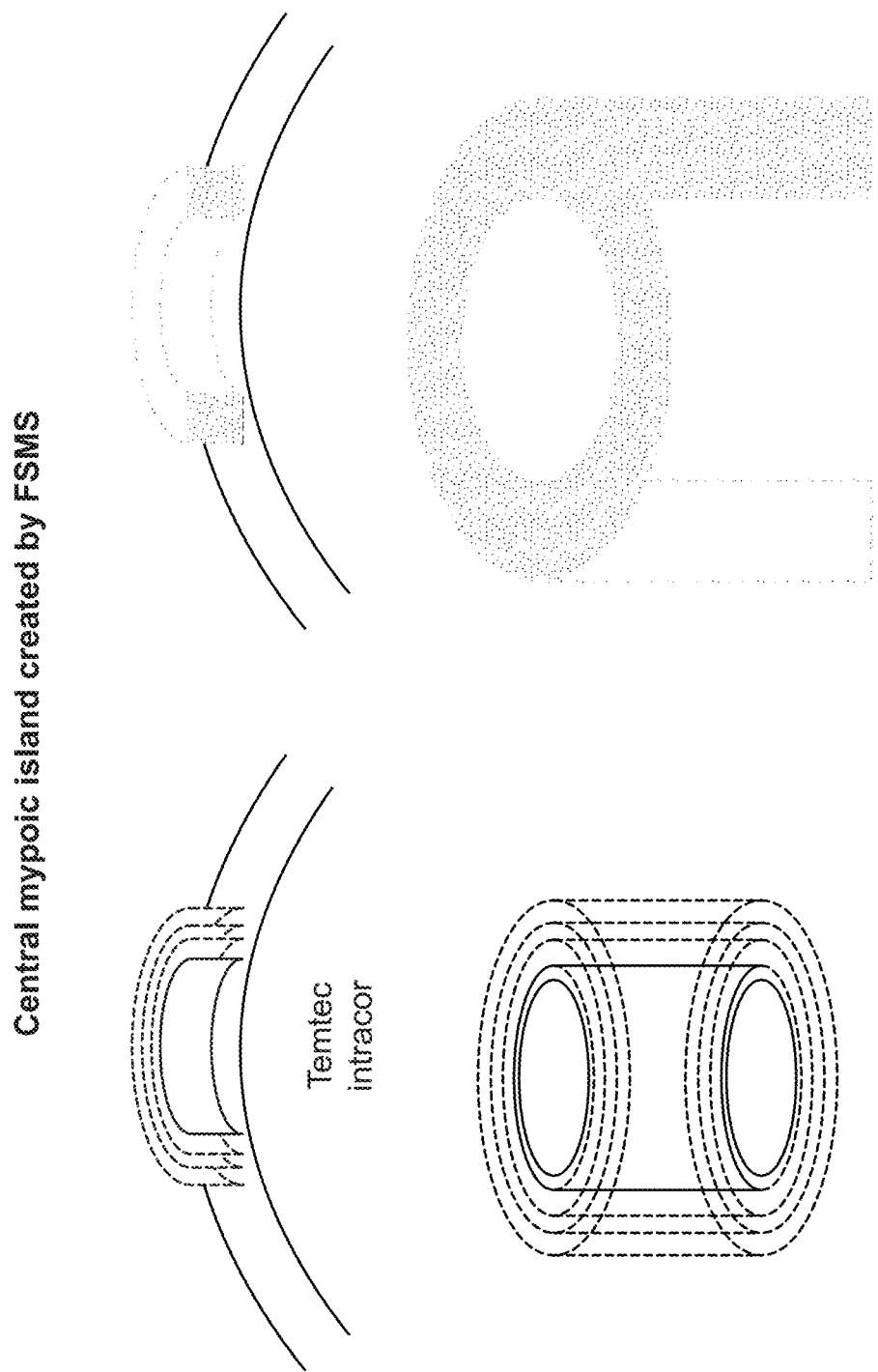
FIG. 10: shows central myopic island created by FSMS.

FIG. 10 represents the central myopic island created by FSMS.

Figure 11:
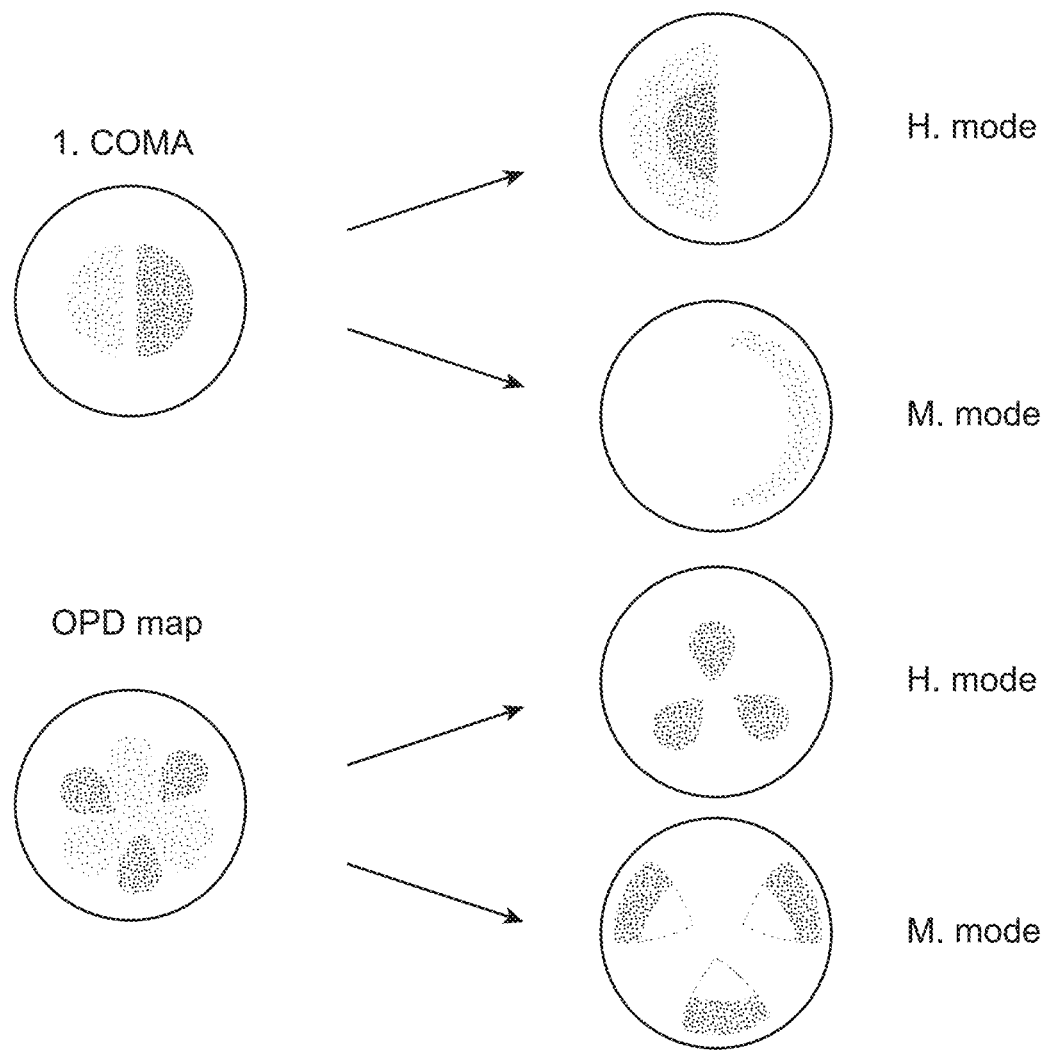
FIG. 11: illustrates FSMS based methods to treat classical aberrations.

5. Use of FSMS to correct optical imaging and aberrations. FIG. 11 describes different classic optical aberrations presented by Zernike. The FSMS treats these aberrations by multi shoots on a special space that can be adapted to mode hypermetropic or myopic.

Figure 12:
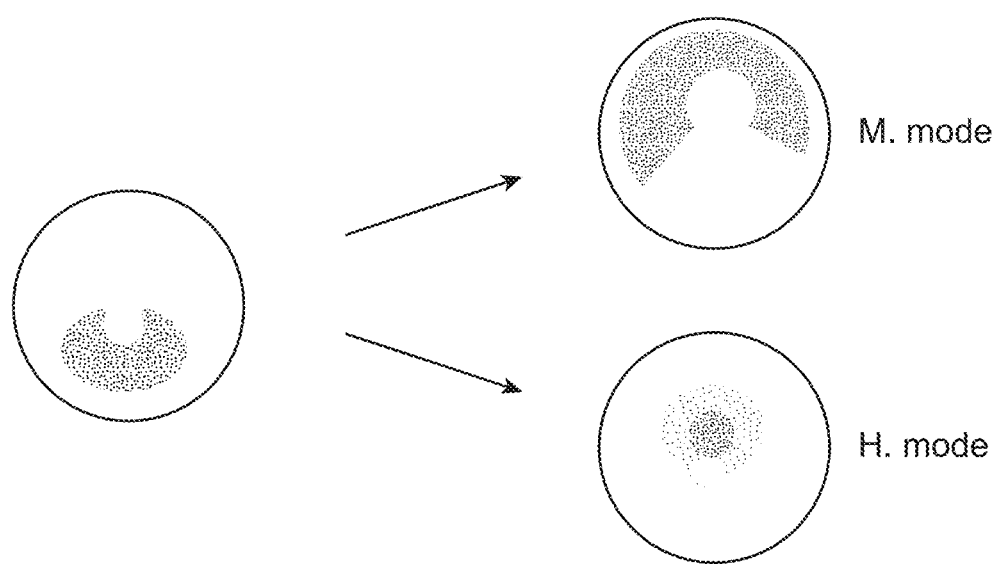
FIG. 12: illustrates FSMS based methods to treat keratoconus.

6. Keratoconus is a degenerative disorder of the eye in which structural changes within the cornea cause it to thin and change to a more conical shape than its normal gradual curve. Keratoconus can cause substantial distortion of vision, with multiple images, streaking and sensitivity to light all often reported by the patient. Similar to the optical aberrations the cornea asymmetry can be corrected using the FSMS in mode M myopic or mode H hypermetropic. FIG. 12 illustrates the femto second laser multishooting in mode M and mode H.

II. Applying Femto Second Multi Shooting to the Crystalline Lens

The crystalline lens is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation; it is similar to the focusing of a photographic camera via movement of its lenses. The lens is flatter on its anterior side.
Lens Structure and Function The lens has three main parts: the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are found only on the anterior side of the lens.

1. Lens Capsule

The lens capsule is a smooth, transparent basement membrane that completely surrounds the lens. The capsule is elastic and is composed of collagen. It is synthesized by the lens epithelium and its main components are Type IV collagen and sulfated glycosaminoglycans (GAGs). The capsule is very elastic and so causes the lens to assume a more globular shape when not under the tension of the zonular fibers, which connect the lens capsule to the ciliary body. The capsule varies from 2-28 micrometers in thickness, being thickest near the equator and thinnest near the posterior pole. The lens capsule may be involved with the higher anterior curvature than posterior of the lens.

2. Lens Epithelium

The lens epithelium, located in the anterior portion of the lens between the lens capsule and the lens fibers, is a simple cuboidal epithelium. The cells of the lens epithelium regulate most of the homeostatic functions of the lens. As ions, nutrients, and liquid enter the lens from the aqueous humor, $Na^+/K^+$ ATPase pumps in the epithelial cells of the lens pump ions out of the lens to maintain appropriate lens osmolarity and volume, with equatorially positioned lens epithelium cells contributing most to this current. The activity of the $Na^+/K^+$ ATPases keeps water and current flowing through the lens from the poles and through the equatorial regions.

3. Lens Fibers

Figure 14:
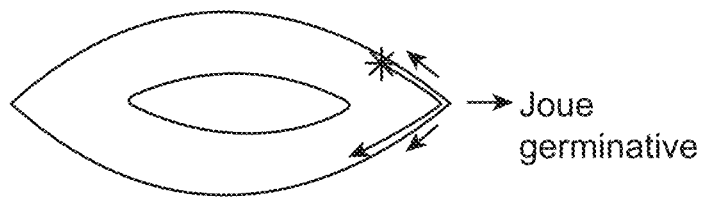
FIG. 14: shows germinative zone of crystalline lens.

The lens fibers form the bulk of the lens. They are long, thin, transparent cells, firmly packed, with diameters typically between 4-7 micrometers and lengths of up to 12 mm. The lens fibers stretch lengthwise from the posterior to the anterior poles and, when cut horizontally, are arranged in concentric layers rather like the layers of an onion. If cut along the equator, it appears as a honeycomb. The middle of each fiber lies on the equator. These tightly packed layers of lens fibers are referred to as laminae. The lens fibers are linked together via gap junctions and interdigitations of the cells that resemble "ball and socket" forms. FIG. 14 illustrates the germinative zone generating cells identical to splice some towards to the capsule anterior or posterior.
Accommodation and Presbyopia Accommodation is a dioptric change in power of the eye that occurs to allow near objects to be focused on the retina. The ability to accommodate is lost with increasing age in humans and monkeys. This phenomenon, called presbyopia, is the most common human ocular affliction, and its pathophysiology remains uncertain. The progressive loss of human accommodative amplitude begins early in life and results in a complete loss of accommodation by age 50 to 55 years. Presbyopia is correctable by various optical means and, although not a blinding condition, its cost in devices, lost productivity, and (more recently), for surgical interventions is considerable. The classic theory of accommodation in humans proposes that the ciliary muscle moves forward and axially in the eye during contraction, releasing tension on the anterior zonular fibers and allowing the lens to become more spherical and thicken axially.1 During disaccommodation, the ciliary muscle relaxes, allowing the elastic choroid to pull the ciliary muscle posteriorly, increasing the tension on the anterior zonules to flatten the lens. Alteration of every component of the accommodative apparatus has been proposed to explain presbyopia. Rhesus monkeys and humans exhibit a similar accommodative mechanism and lens growth throughout life and develop presbyopia with a similar relative age course. Theories to explain the pathophysiology of presbyopia fall into two main categories, involving dysfunction of either the lens or the ciliary muscle.

Numerous publications have been made on the use of a laser to rejuvenate the lens, with the concept of incising the crystalline lens in order to relax the structure. However, the results obtained for presbyopia are to this day disappointing.

The method of the present invention is based on femto second multi shoot laser (FSMS) on the lamellar structure of the crystalline lens with X63 nm.

To be specific, the femto second laser (FSL) is useful in ocular surgeries due to its ultrafast pulses in the range of $10^{-19}$ second and its decreased energy requirements for tissue destruction, allowing for reduced unintended destruction of surrounding tissues. Photodisruption is essentially induced by vaporization of target tissues, which occurs through the following steps: the focused laser energy increases to a level where a plasma is generated; the plasma expands and causes a shock wave, cavitations, and bubble formation; and then the bubble expands and collapses, leading to separation of the tissue.

The prospect of non-invasive therapy involving FSMS X63 nm is applicable to the lens for phaco rejuvenation and presbyopia. It is important to acknowledge the physiology of accommodation and the physiopathology of presbyopia in order to define the top priority in crystalline lens rejuvenation. The core of crystalline lens is the oldest and it exists from embryonic stage; with exposition to the light with time it becomes rigid. In contrast the peripheral layers of the crystalline lenses, are not embryonic are perfectly malleable and keep all their capacity to be responsive to ciliary muscle. It is important that the effect sought by the laser be directed to the central core of the crystalline lens and not the periphery; indeed the current laser techniques are directed to the peripheral layers than the core and isolate even more this central core from the ciliary muscle, which intensifies the presbyopia.

Femto-Phaco Rejuvenation with Close Capsule Using FSMS

The maintenance of the transparency of the crystalline lens is the primary goal of a non-invasive FSMS and can be reached for following reasons:

The integrity of the capsule of the lens, eliminates the conventional phenomena of healing; also lens metabolism being devoid of DNA and RNA and thus of any type of protein; this ensures metabolic neutrality face to "aggression" of the laser.

Figure 13:
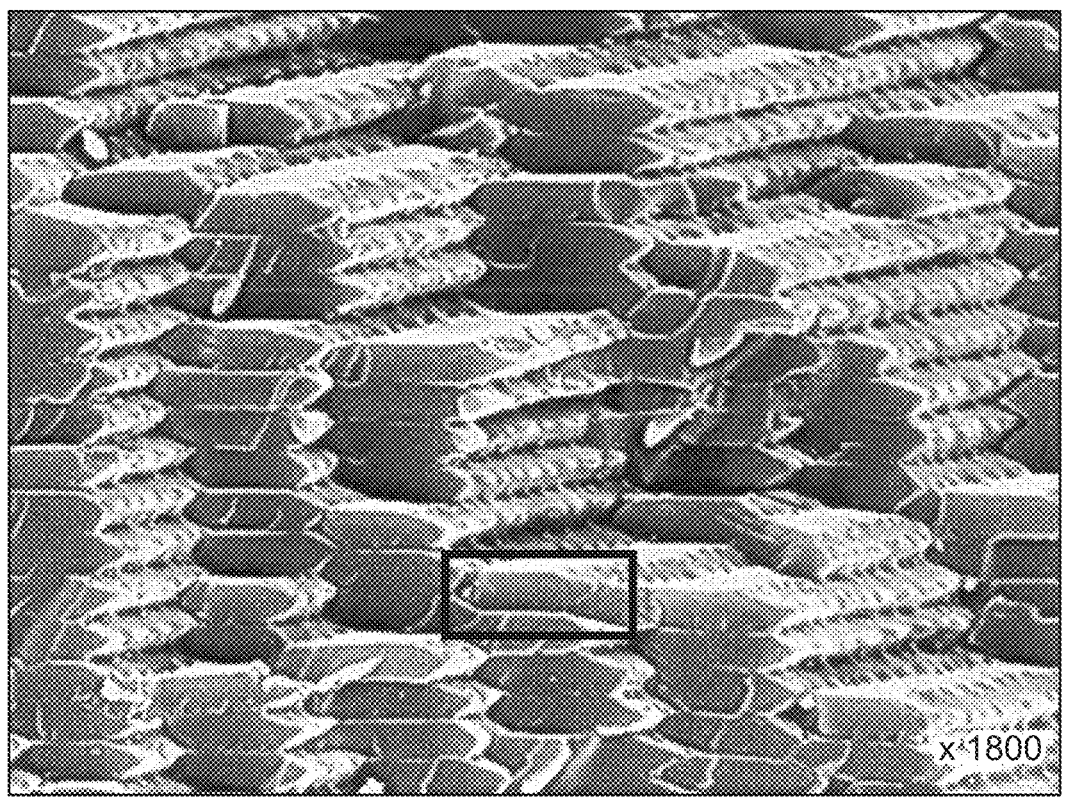
FIG. 13: shows electron microscopic image of the cellular layer of the crystalline lens.

The respect of the cellular and tissue structure and the anatomical features of the crystalline lens is allowing to act on the minor changes of aging, while restoring the accommodative function. FIG. 13 shows an electron microscopic image of the cellular layer of the crystalline lens.

Figure 15:
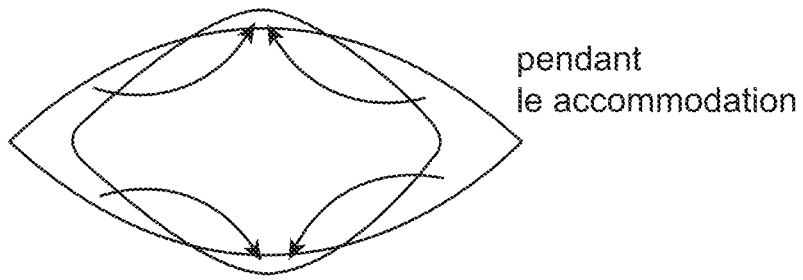
FIG. 15: illustrates volume transfer during accommodation.
Figure 16:
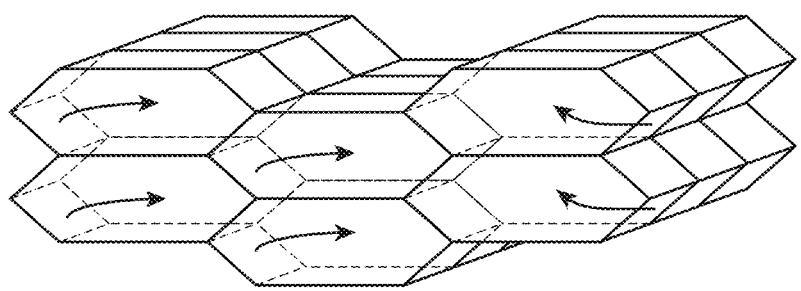
FIG. 16: shows slip assumptions of thickened cells.

The structure in the layer observed by electron microscopy confirms the existence of drift spaces between the layers of cells. The cells are jointed and connected to by their extremities; no inter cellular junction is observed between the layers of cells. The deformability of the crystalline lens under the effect of the ciliary muscle is a consequence of such an anatomical structure. FIG. 15 describes the volume transfer during accommodation and FIG. 16 illustrates slip assumptions of thickened cells.

Methods for Femto-Phaco Rejuvenation Using FSMS

1. Phaco rejuvenation of the crystalline lens before the stage of cataract:

The distribution of impact is done by a no jointed equidistant bombardment of laser impact in the central part of the crystalline lens in order to restore its malleability necessary state for the restitution of its accommodative capacity; the frequency and the density of impacts are variable from center to the periphery of the crystalline lens and used successive times.

2. Phaco delamination by cleavage of tissue structure in overlapping layers of fibrils:

a series of impacts, always non-jointed, generate gas allowing the separation of the crystalline lens in concentric strips with the core, according to its natural structure. The number of drift space carried out can be variable according to the age; to avoid the risk of a capsular rupture the Phaco delamination necessities several treatment of FSMS.

The FSMS Phaco rejuvenation eliminates occurred opacity of the crystalline lens, thus is also a preventive treatment for cataract.

Accommodation Using Techniques of FSMS

The accommodation theory of Helmholtz has been subsequently confirmed by the work of Glasser and Kaufman.

During accommodation the contraction of the ciliary muscle, causes a reduction in its diameter as a sphincter muscle. This movement slackens the zonule and thus the tension exerted on the capsule of the crystalline lens in its equator; this generates a reduction of the equatorial diameter of the crystalline lens, and simultaneously an anteroposterior thickening according to sagittal centers. The internal structure of the lens consists of layers of cells structured like flat ribbons. For the lens to become more spherical it is necessary that a volume of cells moves from the equator towards the poles.

Figure 17:
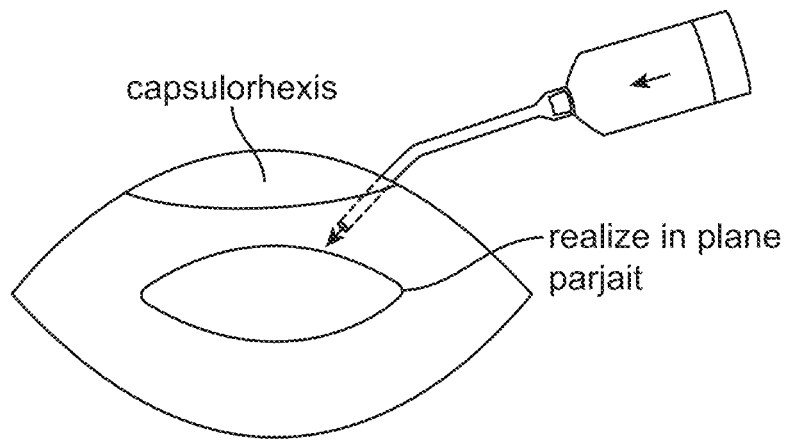
FIG. 17: illustrates hydro dissection
Figure 18:
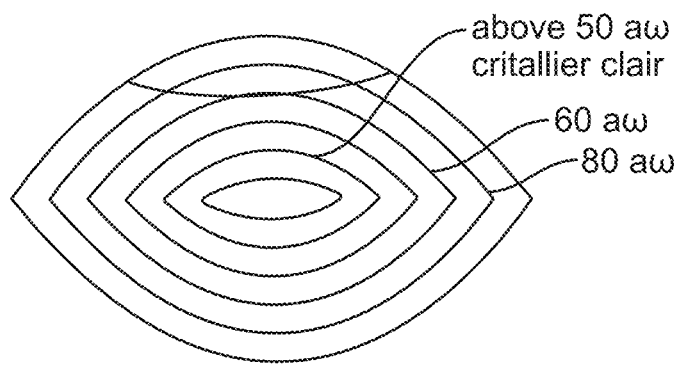
FIG. 18: shows relation of cleavage plan of lens and the age of the patient during cataract surgery.

The hydro dissection during the cataract surgery by jets of BSS, confirmed the absence of connection between the strips; this gap in junctions allows the slip of the cell layers; this movement is possible by a modification of the thickness of the cells and a shortening of the cells keeping a constant volume; only in this case can the equatorial volume relocate towards the poles and vice versa. By observing the cleavage planes during cataract surgery, it is easy to observe their equivalent form to that of the crystalline lens, smaller according to the depth; parallel to the surface and with no obstacles in particular with the level as the cell joining anatomic level; there is no connection between two different planes even in the central core of the lens, before it become too old. Indeed, during the cataract surgery the cleavage plane during the hydro dissection is increasingly far from the center and more towards the periphery depending on the stage of the cataract. FIG. 17 describes the process of hydro-dissection and FIG. 18 shows the relation between age and the zone of the treatment in cataract patients.

The sclerosis of the crystalline lens is accompanied by the adherence of cell layers from the center towards the periphery; this phenomenon is simultaneously responsible for increases of presbyopia.

Techniques

The FSMS possesses an OCT describing with precision the form of the lens and its anatomical position during intervention. During neutralization of accommodation by cyclopegia, the volume and the shape of the lens in space is constant; this form is precisely defined, with each impact of the laser releasing a volume of gas to produce a series of cleavages.

Macroscopic Strategy for FSMS

Figure 19:
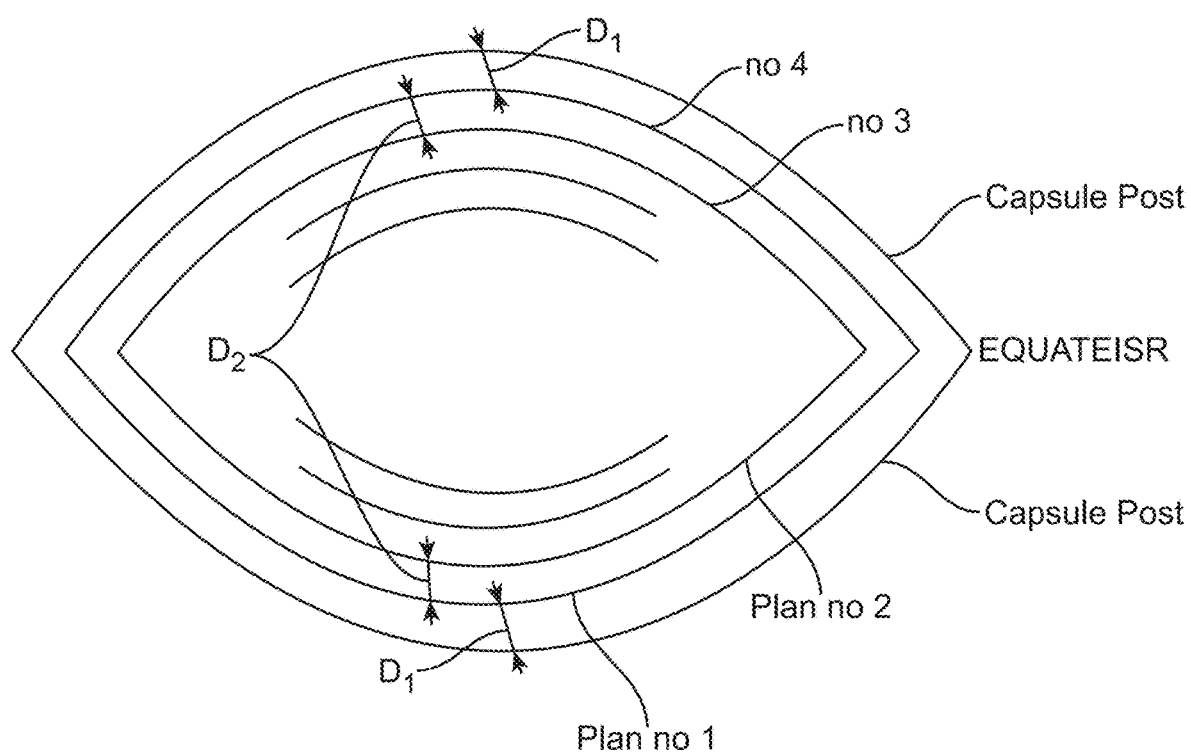
FIG. 19: illustrates a macroscopic strategy.

The Macroscopic Strategy for FSMS consists starting from the major plane, for example with 50 microns in front of the posterior capsule, according to a concave surface parallel with the capsule, a series of equidistant cleavage planes towards the central core of the lens. The distance of the cleavage from the central core of the lens will vary according to the patient's age. The procedure will be repeated, but this time towards surface, according to a convex form parallel with the capsule in the anterior segment side and equidistant with cleavages planes processed in the first phase of the treatment; the result is the creation of virtual spaces that meet at the equator, FIG. 19. Indeed, the thickness of all crystalline lens cells is identical when they have the same age regardless of whether they are situated in an anterior or posterior segment. This allows for obtaining equidistant cleavages from the lens capsule, FIG. 1.

Microscopic Strategy for FSMS

Figure 20:
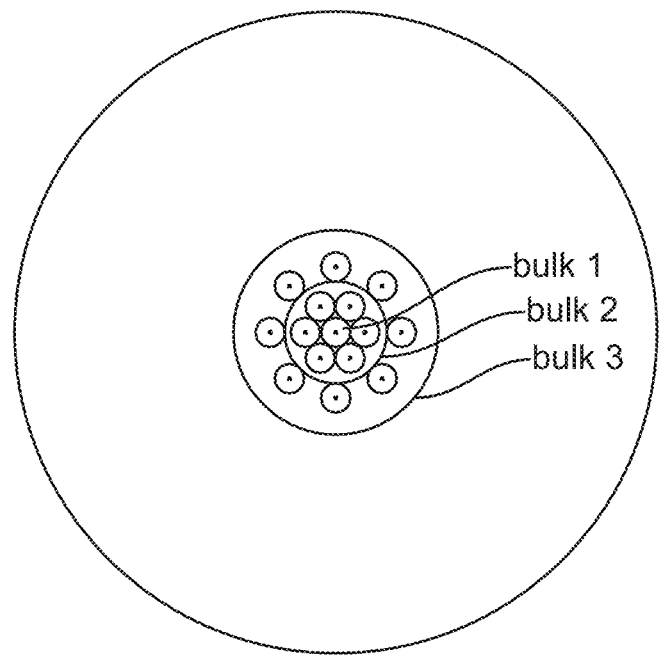
FIG. 20: illustrates a microscopic strategy.

Strategic impacts of laser shoots realize the cleavages. According to this strategy the impacts are distributed: FIG. 20.

Figure 21:
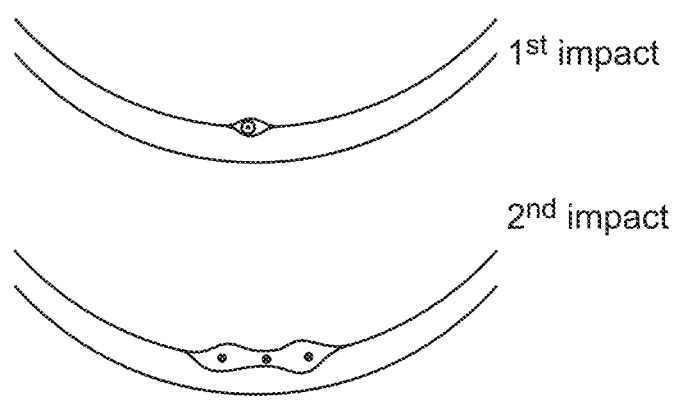
FIG. 21: illustrates the increase of impact diameter by successive laser shoots.

1. The first impact, in the center of considered surface, produces the first gas bubble; the diameter of the bubble is in direct correlation of the choice of the energy level of laser impact chosen.
2. A series of 3 to 5 impacts in a concentric circle, produces the second generation of gas bubbles. The distance between the first impact and the following series of impacts corresponds to the diameter of both half bubbles of first and second generation of gas bubbles.
3. The third circle of impacts with an increase in energy of the FSMS allows the widening of the gas bubble, reducing the number of cleavage planes while increasing the width of the planes.
4. This strategy is similar to archery with the impact of arrows one after the other on a spiral of increasing diameter from the original the impact, FIG. 21.
5. Contrary to the cornea or stroma where the layers of collagen are linked, in the lens, the space created corresponds anatomically to a preexisting slip surface. This strategy of FSMS is totally different from Lasik or corneal flap.

FSMS on Lens Core

In advanced stages of cataract thus aging, the approach of cleavage for accommodation is no longer realistic. In this situation the direct femto second multi shooting is the equivalent strategy of X63 nm, to soften the aged structure.

Combined with the techniques of FSMS of X63 nm in the cornea stroma and FSMS intra crystalline lens, the FSMS is the solution for non-invasive refractive surgery.

What is claimed is:

1. A method of ophthalmic surgery comprising:
generating a plurality of laser bombardments using a FSMS laser;
directing the plurality of laser bombardments towards a corneal stroma structure so that the plurality of laser bombardments respectively impact the cornea in areas between collagen fibers thereby forming a plurality of microvacuoles;
wherein a distance between any two adjacent laser bombardments within the plurality of laser bombardments is equal to an integer multiple of 63 nanometers; and
wherein the plurality of laser bombardments have a varying impact density at different depths of the corneal stroma and thereby treating corneal aberrations.

2. The method of claim 1, wherein the ophthalmic surgery comprises refractive surgery.

3. The method of claim 1, wherein the plurality of laser bombardments decrease links between collagen fibers.

4. The method of claim 3, wherein the plurality of laser bombardments increase the plasticity of the corneal stroma resulting in a reduction of a mechanical resistance to an intraocular pressure.

5. The method of claim 1, comprising orienting the plurality of laser bombardments so that the density of the plurality of laser bombardments increase from a bottom layer of the cornea to an upper layer of the corneal stroma and thereby treating myopia.

6. The method of claim 1, wherein the plurality of laser bombardments treat hyperopia.

7. The method of claim 1, wherein the plurality of laser bombardments create ectasia on an optic zone to treat hyperopia astigmatism.

8. The method of claim 1, wherein the plurality of laser bombardments impact onto an external ring surface of the corneal stroma thereby treating myopia astigmatism.

9. The method of claim 1, wherein the plurality of laser bombardments create a central myopic island for treating presbyopia.

10. The method of claim 1, wherein the plurality of laser bombardments using the FSMS laser reduces destruction of surrounding tissues.

\* \* \* \* \*